US012808807B2

(12) United States Patent
Abu Alsaud et al.

(10) Patent No.: US 12,808,807 B2

(45) Date of Patent: Nov. 24, 2026

(54) LASER INDUCED BREAKDOWN SPECTROSCOPY OF DRILLING CUTTINGS

(71) Applicant: Saudi Arabian Oil Company, Dhahran (SA)

(72) Inventors: Sara Abu Alsaud, Dhahran (SA); Klemens Katterbauer, Dhahran (SA); Abdallah A. AlShehri, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 19/074,959

(22) Filed: Mar. 10, 2025

(65) Prior Publication Data

US 2026/0266731 A1 Sep. 10, 2026

(51) Int. Cl.
*G01N 33/24* (2006.01)
*E21B 21/08* (2006.01)
(Continued)

(52) U.S. Cl.
CPC ......... *G01N 21/718* (2013.01); *E21B 21/085* (2020.05); *G01N 1/4077* (2013.01); (Continued)

(58) Field of Classification Search
CPC ......... G01N 21/718; G01N 2001/4088; G01N 2001/4094; G01J 3/443; E21B 21/085
See application file for complete search history.

(56) References Cited

U.S. PATENT DOCUMENTS 10,324,039 B2 6/2019 Walls
10,598,009 B2 3/2020 Stringer
(Continued)

FOREIGN PATENT DOCUMENTS

CN 201924920 U 8/2011
CN 210585793 U 5/2020
(Continued)

OTHER PUBLICATIONS

Navid Khajehzadeh, "On-stream and quantitative mineral identification of tailing slurries using LIBS technique", 2016 (Year: 2016).*
(Continued)

*Primary Examiner* — Maurice C Smith
(74) *Attorney, Agent, or Firm* — Fish & Richardson P.C.

(57) ABSTRACT

This disclosure describes systems and methods for elemental analysis of rock cuttings in underbalanced coiled tubing drilling. The systems and methods include a laser induced breakdown spectroscopy (LIBS) system; an ultrasonic shaking plate configured to separate rock cuttings from a drilling slurry; and a wireless communications system communicatively coupled to the LIBS system. One or more processors are configured to perform operations including introducing a drilling slurry including powdered rock cuttings to the ultrasonic shaking plate. The ultrasonic shaking plate is operated to separate the powdered rock cuttings from the drilling slurry. One or more recordings are captured of the powdered rock cuttings using the LIBS system. An elemental analysis of the powdered rock cuttings is determined based on the one or more recordings; and the elemental analysis is transmitted to an external computing system by the wireless communications system.

20 Claims, 4 Drawing Sheets

(51) Int. Cl.
*G01N 1/40* (2006.01)
*G01N 21/71* (2006.01)
*G01N 33/00* (2006.01)

(52) U.S. Cl.
CPC ................ *G01N 2001/4088* (2013.01); *G01N 2001/4094* (2013.01); *G01N 33/0091* (2024.05); *G01N 33/24* (2013.01); *G01N 2201/06113* (2013.01)

(56) References Cited

U.S. PATENT DOCUMENTS

| | | | |
|---|---|---|---|
| 11,492,901 B2 | 11/2022 | Elgamal | |
| 11,585,213 B1 | 2/2023 | Tonner et al. | |
| 11,688,172 B2 | 6/2023 | Ruel et al. | |
| 11,753,884 B2 | 9/2023 | Blue, III et al. | |
| 11,788,408 B2 | 10/2023 | Ismailova et al. | |
| 11,822,039 B2 | 11/2023 | Hird et al. | |
| 12,012,852 B1 | 6/2024 | Tonner et al. | |
| 2013/0271761 A1 | 10/2013 | Rutberg et al. | |
| 2018/0188225 A1 | 7/2018 | Viscarra et al. | |
| 2020/0377821 A1* | 12/2020 | Sikora | B08B 3/04 |

FOREIGN PATENT DOCUMENTS

| | | | | |
|---|---|---|---|---|
| CN | 210714534 U | | 6/2020 | |
| CN | 112196483 A | | 1/2021 | |
| CN | 112642704 A | * | 4/2021 | B01D 19/0078 |
| CN | 113027364 A | | 6/2021 | |
| CN | 113027436 A | | 6/2021 | |
| CN | 214532942 U | | 10/2021 | |
| CN | 115711772 A | | 2/2023 | |
| CN | 115943302 A | | 4/2023 | |
| CN | 117225782 A | | 12/2023 | |
| EP | 3156587 A1 | | 4/2017 | |

OTHER PUBLICATIONS

Kerstin Kuhn, "Chemical mapping of mine waste drill cores with laser-induced breakdown spectroscopy (LIBS) and energy dispersive X-ray fluorescence (EDXRF) for mineral resource exploration" Nov. 2015 (Year: 2015).*

El Meguid et al., "Novel Engineering Approach Utilizing Underbalanced Coil Tubing Drilling Solutions for Tight Sour Gas Carbonate," Paper presented at the ADIPEC, Abu Dhabi, UAE, Oct. 2022, Abstract Only, 2 pages.

Fabre, "Advances in Laser-Induced Breakdown Spectroscopy analysis for geology: A critical review," Spectrochimica Acta Part B: Atomic Spectroscopy, Apr. 2020, 166(105799): 1-16.

Georgi et al., "Advances In Cuttings Collection And Analysis," Paper presented at the SPWLA 34th Annual Logging Symposium, Calgary, Alberta, Jun. 1993, Abstract Only, 1 page.

Harmon et al., "Laser-Induced Breakdown Spectroscopy—A geochemical tool for the 21st century," Applied Geochemistry, May 2021, 128(104929):1-55.

Harmon et al., "Laser-induced breakdown spectroscopy—An emerging chemical sensor technology for real-time field-portable, geochemical, mineralogical, and environmental applications," Applied Geochemistry, May 2006, 21(5):730-747, 18 pages.

Huang et al., "Rapid detection and identification of rocks and minerals by laser-induced breakdown spectroscopy," Microw Opt Technol Lett., 2023, 65:1439-1447, 9 pages.

Matanovi et al., "Underbalanced Drilling with Coiled Tubing," Paper presented at the Abu Dhabi International Petroleum Exhibition and Conference, Abu Dhabi, United Arab Emirates, Oct. 2000, Abstract Only, 1 page.

Pace et al., "Analysis of Minerals and Rocks by Laser-Induced Breakdown Spectroscopy," Spectroscopy Letters, 2011, 44:399-411.

Tonner et al., "Automation Provides Unique Insights of The Rock Record and Subsurface Through the Delivery of a Robotic Sample Collection and Analysis Device," Annual Convention & Exhibition, May 20-23, 2018, 8 pages.

Ytsma et al., "Accuracies and detection limits of major, minor, and trace element quantification in rocks by portable laser-induced breakdown spectroscopy," Spectrochimica Acta Part B: Atomic Spectroscopy, Sep. 2020, 171(105946):1-17.

International Search Report and Written Opinion in Intl. Appln. No. PCT/US2026/018340, mailed on Jul. 6, 2026, 13 pages.

* cited by examiner

LASER INDUCED BREAKDOWN SPECTROSCOPY OF DRILLING CUTTINGS

TECHNICAL FIELD

The present disclosure relates to characterizing drilling cuttings using laser induced breakdown spectroscopy.

BACKGROUND

Underbalanced coiled tubing drilling (UBCTD) is a drilling method that can be used to drill wells to recover natural gas from depleted reservoirs. Underbalanced drilling involves maintaining the pressure in the wellbore lower than the pressure in the subsurface formation. Coiled tubing is a continuous length of steel or composite tubing that is wound onto a reel. UBCTD operations reduce the risk of damaging the subsurface formation by avoiding heavy drilling fluids, and do not require a full-scale drilling rig.

Underbalanced coiled tubing drilling (UBCTD) has become a valuable asset in enhancing hydrocarbon productivity and recovery through the usage of non-invasive fluid while drilling and reducing future workover stimulation costs, sidetracking, and drill string differential sticking events. Since underbalanced conditions induces fluid influx from the reservoir to the wellbore, UBCTD gives an excellent indication of the hydrocarbon presence in the targeted zones.

SUMMARY

Under balanced coil tubing drilling (UBCTD) can be used for drilling wells with extra slimholes (e.g., boreholes with a diameter less than 4 inches, or typically 3⅝ inches). Due to the small diameter of the borehole, UBCTD has limited formation evaluation and logging capabilities. One safe, surface available method uses rock cuttings for geo-navigation and steering of laterals to land in a target productive zone. The collection and analyzing of the rock cuttings affect the accuracy of correlating the cuttings to the appropriate depth as well as the stratigraphic resolution of interpreted layers.

This disclosure describes systems and methods for characterizing drilling cuttings in UBCTD operations. An automatic laser induced breakdown spectroscopy (LIBS) system can be used for elemental analysis of rock cuttings. A drilling slurry is introduced to an ultrasonic shaking plate to separate the rock cuttings from the drilling slurry. The LIBS system can capture one or more recordings of the rock cuttings. Based on the one or more recordings, an elemental analysis of the rock cuttings is generated. The elemental analysis can be wirelessly transmitted to an external computing system for use, for example, to geo-steer the UBCTD drill. The wireless communications system can include low latency elements that can transfer large amounts of data in real-time.

Implementations of the systems and methods of this disclosure can provide various technical benefits. These systems and methods can deliver full elemental analysis on rock cuttings in a drilling operation in real time by leveraging robotic and automation technologies together with internet of things (IoT). Using wireless communication enables efficient transfer from multiple sensors without the need to have physical connections providing more flexibility in layout and positioning the sensors. Additionally, the systems and methods have improved reliability and robustness to damages compared to a wired system because there are not physical cables between units that could be damaged. The wireless sensor communication utilizes a low-latency communication architecture that enables fast and rapid communication between the sensor devices and the server as well as real-time field unit data interpretation. The systems and method of this disclosure provide efficient data communication, and the LIBS system and ultrasonic shaking plate can provide solid chemical analysis on most or all rock cuttings extracted from the subsurface formation.

The details of one or more embodiments of these systems and methods are set forth in the accompanying drawings and the description below. Other features, objects, and advantages of these systems and methods will be apparent from the description and drawings, and from the claims.

DESCRIPTION OF DRAWINGS

Like reference symbols in the various drawings indicate like elements.

DETAILED DESCRIPTION

Under balanced coil tubing drilling (UBCTD) can be used for drilling wells with extra slimholes (e.g., boreholes with a diameter less than 4 inches, or typically 3⅝ inches). Due to the small diameter of the borehole, UBCTD has limited formation evaluation and logging capabilities. One safe, surface available method uses rock cuttings for geo-navigation and steering of laterals to land in a target productive zone. The collection and analyzing of the rock cuttings affect the accuracy of correlating the cuttings to the appropriate depth as well as the stratigraphic resolution of interpreted layers.

This disclosure describes systems and methods for characterizing drilling cuttings in UBCTD operations. An automatic laser induced breakdown spectroscopy (LIBS) system can be used for elemental analysis of rock cuttings. A drilling slurry is introduced to an ultrasonic shaking plate to separate the rock cuttings from the drilling slurry. The LIBS system can capture one or more recordings of the rock cuttings. Based on the one or more recordings, an elemental analysis of the rock cuttings is generated. The elemental analysis can be wirelessly transmitted to an external computing system for use, for example, to geo-steer the UBCTD drill. The wireless communications system can include low latency elements that can transfer large amounts of data in real-time.

Figure 1:
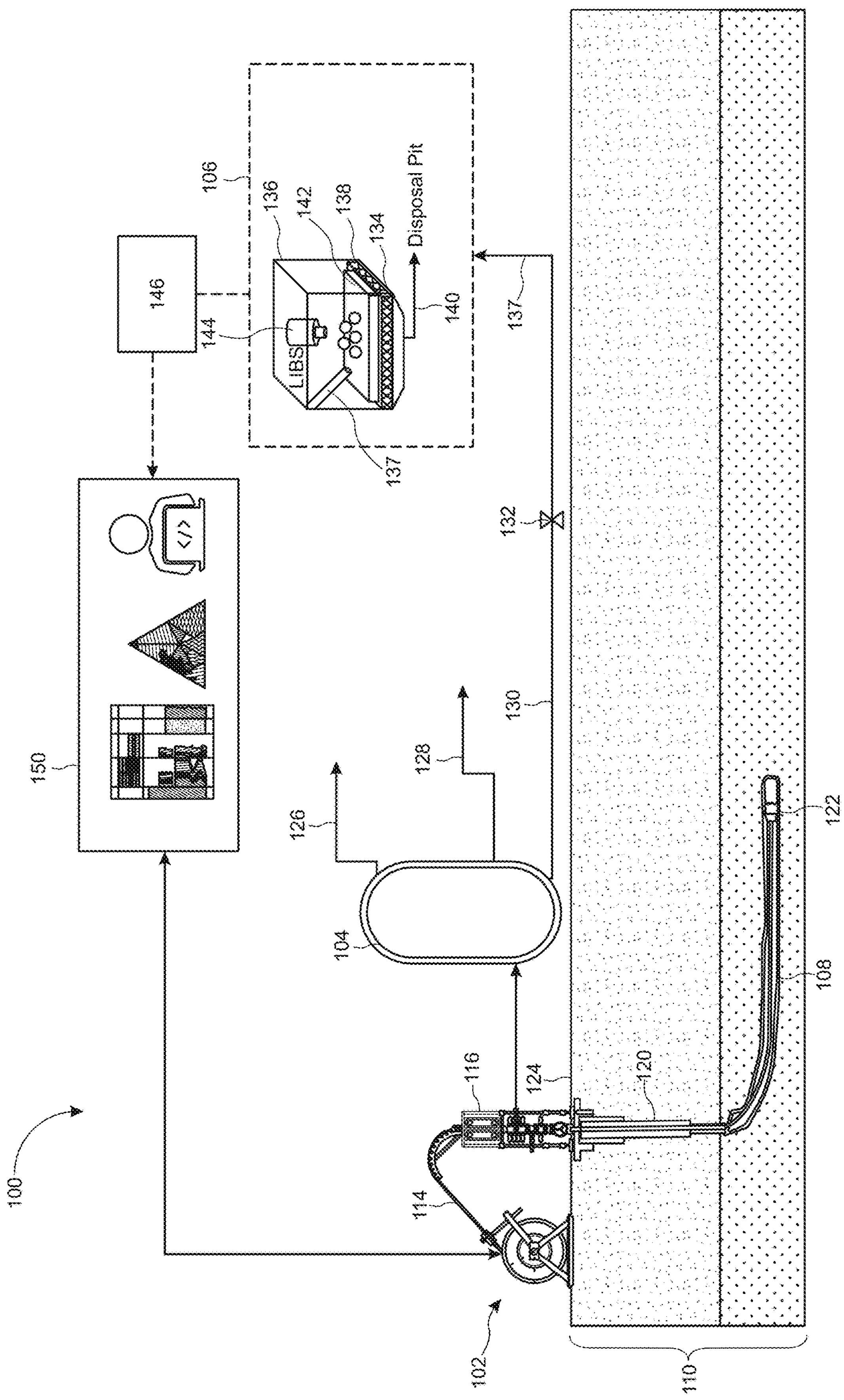
FIG. 1 is a schematic diagram of an example system for characterizing rock cuttings in a UBCTD operation.

FIG. 1 illustrates an example UBCTD drilling operation 100. The UBCTD drilling operation 100 includes a coiled tubing drilling unit 102, a phase separator 104, and a cuttings analyzer 106. The coiled tubing drilling unit 102 is drilling a lateral well 108 in the subsurface formation 110.

The coiled tubing drilling unit 102 includes a tubing reel 112 on which the coiled tubing 114 is wrapped. The coiled tubing extends from the tubing reel 112 through an injection head 116 and wellhead 118 into the main wellbore 120. A bottom hole assembly 122 is attached at the end of the coiled tubing 114. The bottom hole assembly 122 includes a drill bit, a motor, and a steering tool to steer the bottom hole assembly 122. In some implementations, the bottom hole assembly 122 can include logging while drilling tools that can measure properties of the subsurface formation 110 while the well lateral 108 is being drilled. However, in UBCTD, the availability of logging-while-drilling tools is limited, as compared with conventional drilling, due to the small borehole size and the aggressive dynamic operating conditions in the well bore. Power and communication cables extend from the bottom hole assembly 122 through the coiled tubing 114 to the surface 124. The communication cables enable bi-directional communication between the bottom hole assembly 122 and a control system 150 at the surface 124.

The phase separator 104 receives drilling fluids from the wellbore 120. In UBCTD, hydrocarbons and/or other fluids can be produced to the surface 124 from the subsurface formation 110 because the pressure in the well 108 is less than the formation pressure. The phase separator 104 separates the drilling fluids into a gas phase 126, a condensate phase 128, and a drilling fluid slurry 130 that includes rock cuttings. The gas phase 126 can be sent to a flare stack or a production line to a gas plant. Similarly, the condensate 128 can be sent to a green burner for flaring or to an export line. The drilling fluid slurry 130 including powdered rock cuttings is sent to the cuttings analyzer 106. A pump suction and flowline control valve 132 is positioned between the phase separator 104 and the cuttings analyzer 106 to control the flow of drilling fluid slurry 130 to the cuttings analyzer 106.

Positioning the cuttings analyzer 106 downstream of the phase separator 104 is advantageous to increase the safety of collecting rock cuttings and enable continuous collection of rock cuttings. In conventional systems, the rock cuttings are taken directly from a sample catching chamber controlled by a valve before the gas has been separated from the drilling slurry. The valve is kept open for discrete periods of time for safety consideration (e.g., to avoid buildup of hydrocarbons in the sample catching chamber).

The cuttings analyzer 106 includes an ultrasonic shaking plate 134 positioned within a chamber 136. Drilling slurry can be introduced to the ultrasonic shaking plate 134 through the extraction line 137. The ultrasonic shaking plate 134 can be automatically controlled (e.g., by a control system or computer system) to shake the rock cuttings to separate the rock cuttings from the drilling slurry. The ultrasonic shaking plate 134 includes a sieve 138 to remove excess drilling fluid from the rock cuttings. The sieve can have a mesh size in the range of 20 to 150, where the mesh size represents the number of openings in the mesh per linear inch. Alternatively, the mesh can have openings that are between 89 and 850 micrometers (μm) wide. The excess drilling fluid is drained through a flow line 140 to a disposal pit. In some implementations, a fabric-based sheet 142 can be placed on top of the sieve 138. The fabric-based sheet 142 can be a cotton fabric, for example, with holes between filaments or threads of the fabric having smaller dimensions than the mesh size of the sieve 138. The fabric-based sheet 142 can stop rock cuttings from draining with the drilling fluid to the disposal pit. The rock cuttings can be easily removed from the fabric-based sheet 142 as the rock cuttings do not adhere to the fabric.

The cuttings analyzer 106 also includes a laser-induced breakdown spectroscopy (LIBS) system 144. LIBS is an analytical technique used to determine the elemental composition of a sample (e.g., rock cuttings). A short duration laser pulse from a high-powered laser (e.g., an Nd: YAG laser) is focused onto the sample. When the energy in the laser pulse surpasses the optical breakdown threshold of the sample material, a plasma is formed on the sample's surface. The plasma emits light as it cools. The emitted light is captured or recorded by a spectrometer that separates the light into its component wavelengths forming spectral data. The emitted light includes spectral lines that are characteristic of the elements in the sample. The spectral data can be processed and interpreted to determine an elemental analysis or composition of the sample. The elemental analysis can be provided in real-time enabling the cuttings analyzer 106 to provide a continuous stream of data regarding the elemental composition of the subsurface to an end-user (e.g., drill operator or technician).

The LIBS system 144 is positioned to take measurements of the rock cuttings on the ultrasonic shaking plate 134. As a rock cutting is being shaken by the ultrasonic shaking plate 134, the LIBS system 144 is able to capture recordings from multiple sides of the rock cutting that can be used to from a three-dimensional (3D) image of the rock cutting. Movements of the ultrasonic shaking plate 134 can be small relative to the focal point of the laser such that the movement of the ultrasonic shaking plate 134 does not degrade the quality of the measurements by moving the rock cuttings out of the focal point. The 3D image is useful for measuring sizes, abrasions, and other elements of the rock cuttings. The LIBS system 144 can generate a distance measurement based on the ablation of the plasma and the reflections from the plasma. The distance measurement in the ablation spectrum can be used to determine the distance to the measurement point on the rock cuttings. By generating multiple distance measurements, the LIBS system can form a 3D image in terms of depth elevation of the rock cuttings.

In some implementations, the LIBS system 144 can take measurements at several positions within the chamber 136. For example, the LIBS system 144 can take measurements in a pre-defined pattern of positions. In some implementations, the LIBS system 144 is controlled by a control system to move the laser to improve a measurement quality of the LIBS system 144.

The cuttings analyzer 106 is in electronic communication with the control system 150 through wireless communications system 146. The cuttings analyzer 106 can wirelessly transmit the image data and elemental analysis to the control system 150 for real-time geosteering monitoring and decision making to enhance the progress of the lateral 108 and further analyze the cuttings (e.g., analyze the cuttings in 3D). The control system 150 can adjust the frequency of collection of spectral data based the drilling conditions such as Rate of penetration (ROP). In addition, the wavelength analysis from the data is stored to enhance and calibrate the imaging characterization and description quality. For example, the wavelength of the laser source changes the measurement spectrum of the reflection, going into infrared (IR) or other regions of the electromagnetic spectrum. The ablation spectrum for various elements is different, and thus performing the wavelength analysis enables fine-tuning of the imaging characterization and description quality.

Figure 2:
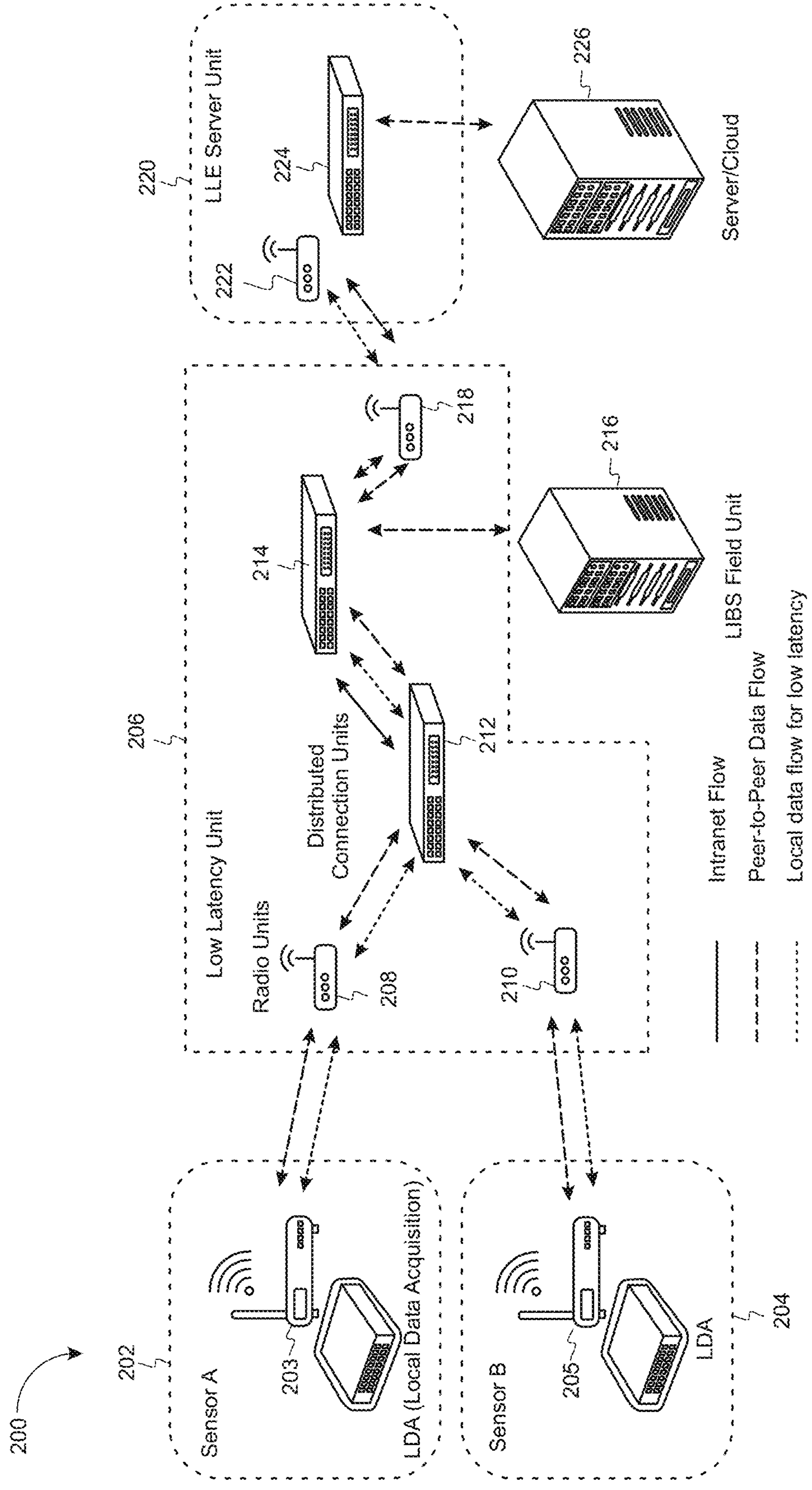
FIG. 2 is a schematic diagram of an example wireless communications system.

FIG. 2 is a schematic of an example architecture for a wireless communication system 200 for use with a LIBS system (e.g., LIBS system 144). The system 200 includes two sensors 202, 204 with transceivers 203, 205 in wireless communication with a base station 206. The sensors 202, 204 perform local data acquisition (LDA), and transmit the data to the base station 206 using peer-to-peer data flows and/or local data flows for low latency. The sensors 202, 204 can be for example photodiodes or camera sensors in the LIBS system that collect the light emitted from the plasma. In some implementations, the system 200 can include one or more sensor, two or more sensors, five or more sensors, or ten or more sensors.

The base station 206 includes transceivers 208, 210 to receive data from and transmit data to the sensors 202, 204, respectively. The transceivers are linked to distributed connection units 212, 214. The distributed connection units 212, 214 can receive and transmit data using an intranet data connection, a peer-to-peer data connection, and/or a low latency local data connection. using a peer-to-peer data connection. The distributed connection units 212, 214 can process and forward data from the sensors 202, 204 to the LIBS field unit 216. The LIBS field unit 216 controls the distributed control units 212, 214. The LIBS field unit 216 can store and process the spectral data captured by the sensors 202, 204. The LIBS field unit 216 can also perform the elemental analysis. The distributed connection unit 214 can transmit data to or receive data from an external computing system 220, such as a link-level encryption (LLE) server unit, via transceiver 218. For example, the distributed connection units 212, 214 can transfer data to the external computing system 220 using a peer-to-peer data connection.

The external computing system 220 receives data from the base unit 206 via transceiver 222. For example, the base unit 206 can transfer elemental analyses, images, and/or raw spectral data to the external computing system 220. The external computing system 220 includes a distributed connection unit 224 that can forward data to a server 226. In some implementations, the server 226 is a cloud based server. The external computing system 220 can include a control system for a drilling rig (e.g., control system 150). The control system can control drilling parameters of the drilling rig, and in response to receiving the data from the base unit 206, the control system can determine new drilling parameters.

The wireless communication between the sensors 202, 204, the base station 206, and the external computing system 220 can utilize the IEEE 802.11 standard for wireless communication that enables fast transfer of real-time data between the sensor and the base station. Using wireless communication enables efficient transfer from multiple sensors 202, 204 without the need to have physical connections thereby providing more flexibility in the layout and positioning of the sensors. Additionally, the system 200 has improved reliability and robustness to damages compared to a wired system because there are not physical cables between units that could be damaged. The wireless sensor communication system from the LIBS based system utilizes a low-latency communication architecture that enables fast and rapid communication between the sensor devices and the server as well as real-time field unit data interpretation.

Real-time or near real-time processing and/or communication refers to a scenario in which received data (e.g., spectral data) are processed as made available to systems and devices requesting those data immediately (e.g., within milliseconds, tens of milliseconds, or hundreds of milliseconds) after the processing of those data are completed, without introducing data persistence or store-then-forward actions. In this context, a wireless communications system is configured to process spectral data as it arrives and transmit an elemental analysis as quickly as possible (though processing latency may occur). Though data can be buffered between module interfaces in a pipelined architecture, each individual module operates on the most recent data available to it. The overall result is a workflow that, in a real-time context, receives a data stream (e.g., spectral data) and outputs processed data (e.g., elemental analysis) based on that data stream in a first-in, first out manner. However, non-real-time contexts are also possible, in which data are stored (either in memory or persistently) for processing at a later time. In this context, modules of the data processing system do not necessarily operate on the most recent data available.

Figure 3:
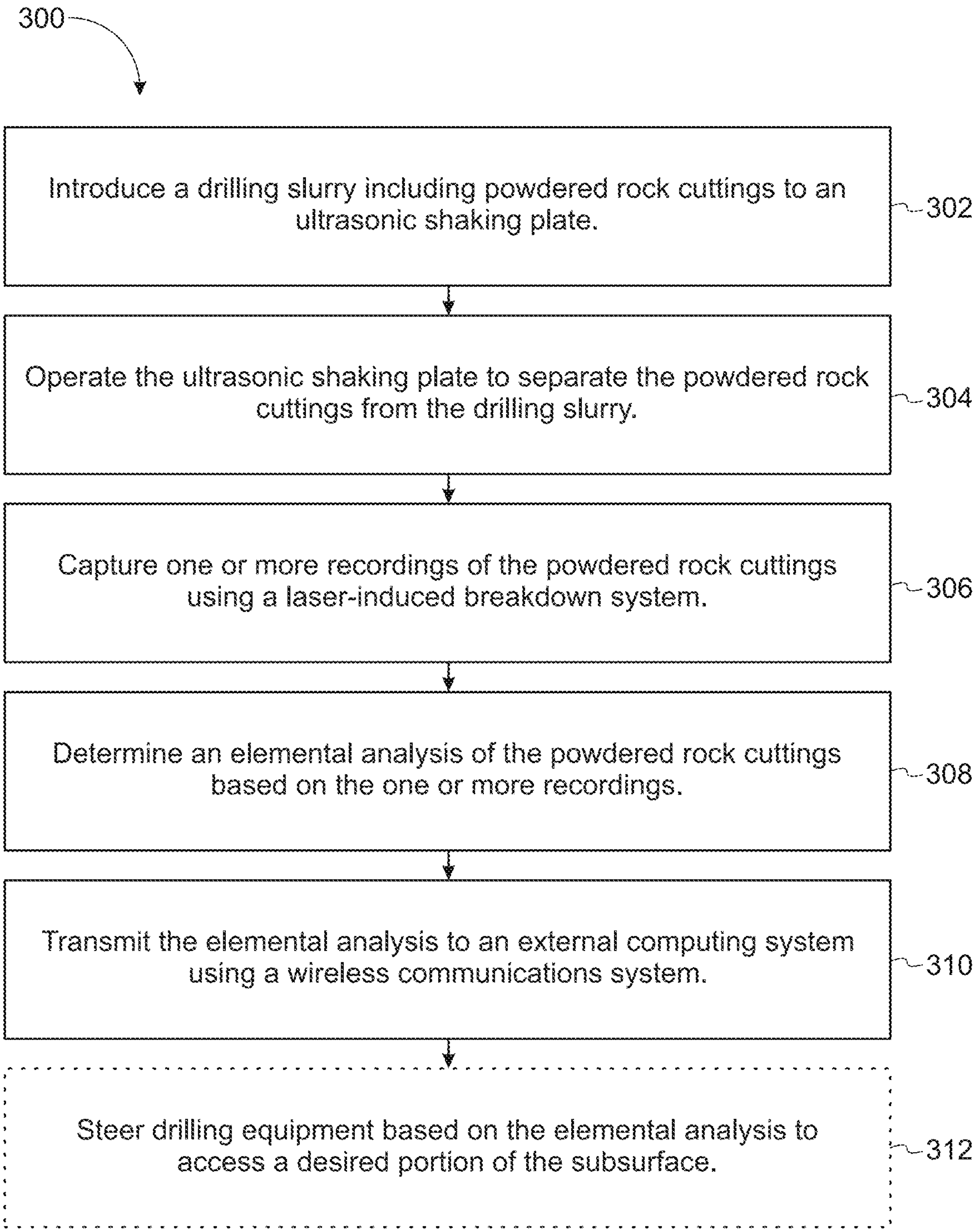
FIG. 3 is a flow chart of an example method for characterizing rock cuttings in a UBCTD operation.

FIG. 3 is a flow chart for an example method 300 for characterizing rock cuttings in a UBCTD operation. A drilling slurry is introduced to an ultrasonic shaking plate (step 302). The drilling slurry includes powdered rock cuttings. The drilling slurry can be introduced to the ultrasonic shaking plate by controlling one or more valves to enable the drilling slurry to flow to the ultrasonic shaking plate. The ultrasonic shaking plate is operated to separate the powdered rock cuttings from the drilling slurry (step 304). A fabric-based sieve can be coupled to the ultrasonic shaking plate to filter the powdered rock cuttings from the drilling slurry.

One or more recordings of the powdered rock cuttings are captured using a LIBS system (step 306). The frequency of capturing the one or more recordings of the powdered rock cuttings can be determined based on drilling conditions of the UBCTD operation. An elemental analysis of the powdered rock cuttings is determined based on the one or more recordings (step 308). A wireless communications system transmits the elemental analysis to an external computing system (step 310). In some implementations, the wireless communications system includes low latency units for fast data transmission from the LIBS system to the external computing system. In some implementations, the elemental analysis is transmitted in real-time.

In some implementations, one or more 3D images of the powdered rock cuttings are generated based on the one or more recordings from the LIBS system. For example, a 3D image can be generated by combining images of each side of a rock cutting. The size of a rock cutting can be determined using the one or more 3D images.

In some implementations, drilling equipment is steered based on the elemental analysis to access a desired portion of the subsurface (step 312). Steering the drilling equipment can include determining that a type of rock of the powdered rock cuttings does not match a type of rock in the desired portion of the subsurface, and in response, steering the drilling equipment to change a direction of drilling. For example, the direction of drilling can be changed to a direction that will encounter the desired portion of the subsurface. Alternatively, if the determined type of rock of the rock cuttings is the type of rock in the desired portion of the subsurface, the drilling equipment can maintain its then-current course.

Figure 4:
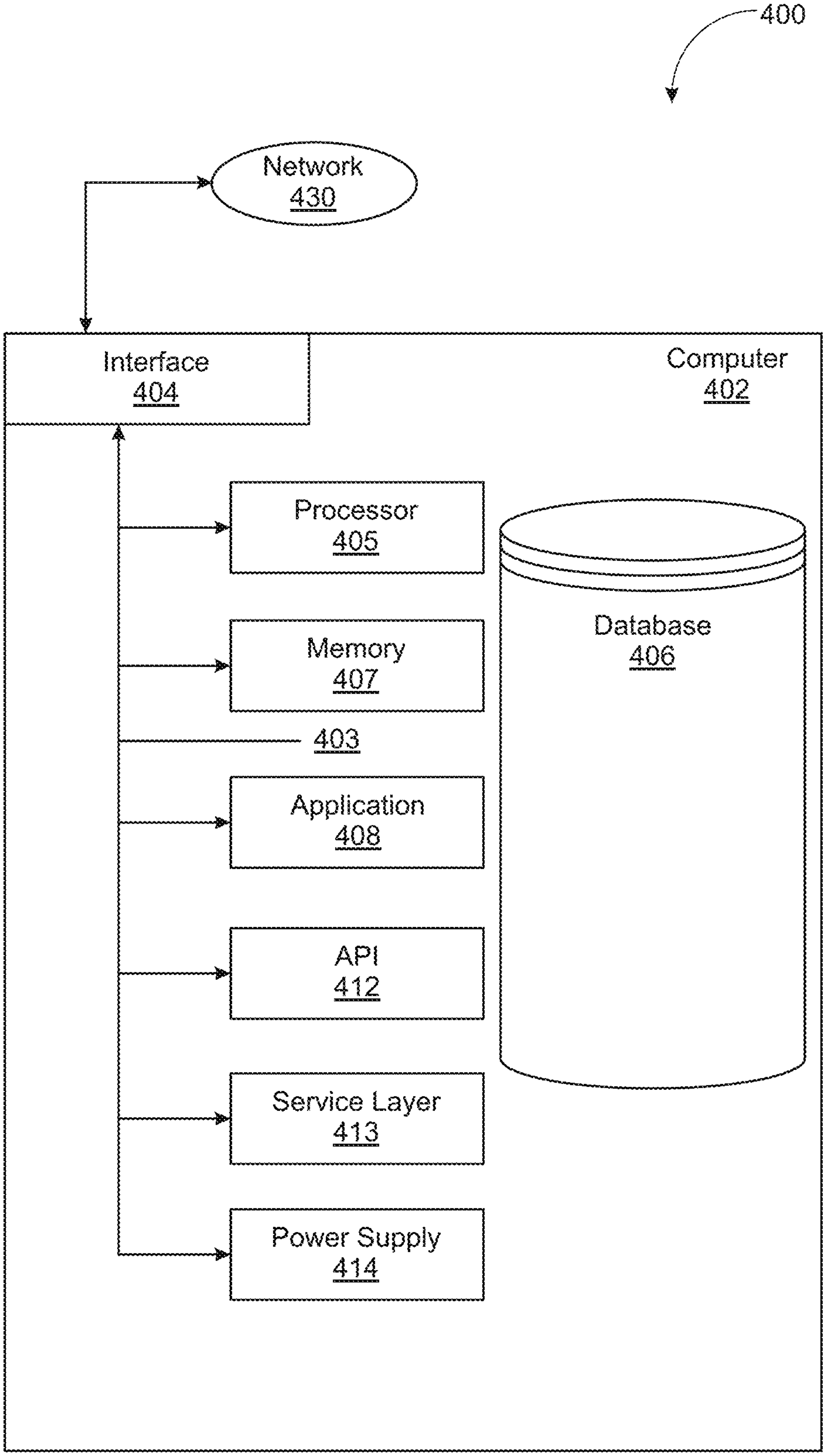
FIG. 4 is a block diagram illustrating an example computer system used to provide computational functionalities associated with described algorithms, methods, functions, processes, flows, and procedures according to some implementations of the present disclosure.

FIG. 4 is a block diagram of an example computer system 400 used to provide computational functionalities associated with described algorithms, methods, functions, processes, flows, and procedures described in the present disclosure, according to some implementations of the present disclosure. The illustrated computer 402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 402 can include input devices such as keypads, keyboards, and touch screens that can accept user information. Also, the computer 402 can include output devices that can convey information associated with the operation of the computer 402. The information can include digital data, visual data, audio information, or a combination of information. The information can be presented in a graphical user interface (UI) (or GUI).

The computer 402 can serve in a role as a client, a network component, a server, a database, a persistency, or components of a computer system for performing the subject matter described in the present disclosure. The illustrated computer 402 is communicably coupled with a network 430. In some implementations, one or more components of the computer 402 can be configured to operate within different environments, including cloud-computing-based environments, local environments, global environments, and combinations of environments.

At a high level, the computer 402 is an electronic computing device operable to receive, transmit, process, store, and manage data and information associated with the described subject matter. According to some implementations, the computer 402 can also include, or be communicably coupled with, an application server, an email server, a web server, a caching server, a streaming data server, or a combination of servers.

The computer 402 can receive requests over network 430 from a client application (for example, executing on another computer 402). The computer 402 can respond to the received requests by processing the received requests using software applications. Requests can also be sent to the computer 402 from internal users (for example, from a command console), external (or third) parties, automated applications, entities, individuals, systems, and computers.

Each of the components of the computer 402 can communicate using a system bus 403. In some implementations, any, or all of the components of the computer 402, including hardware or software components, can interface with each other or the interface 404 (or a combination of both), over the system bus 403. Interfaces can use an application programming interface (API) 412, a service layer 413, or a combination of the API 412 and service layer 413. The API 412 can include specifications for routines, data structures, and object classes. The API 412 can be either computer-language independent or dependent. The API 412 can refer to a complete interface, a single function, or a set of APIs.

The service layer 413 can provide software services to the computer 402 and other components (whether illustrated or not) that are communicably coupled to the computer 402. The functionality of the computer 402 can be accessible for all service consumers using this service layer. Software services, such as those provided by the service layer 413, can provide reusable, defined functionalities through a defined interface. For example, the interface can be software written in JAVA, C++, or a language providing data in extensible markup language (XML) format. While illustrated as an integrated component of the computer 402, in alternative implementations, the API 412 or the service layer 413 can be stand-alone components in relation to other components of the computer 402 and other components communicably coupled to the computer 402. Moreover, any or all parts of the API 412 or the service layer 413 can be implemented as child or sub-modules of another software module, enterprise application, or hardware module without departing from the scope of the present disclosure.

The computer 402 includes an interface 404. Although illustrated as a single interface 404 in FIG. 4, two or more interfaces 404 can be used according to particular needs, desires, or particular implementations of the computer 402 and the described functionality. The interface 404 can be used by the computer 402 for communicating with other systems that are connected to the network 430 (whether illustrated or not) in a distributed environment. Generally, the interface 404 can include, or be implemented using, logic encoded in software or hardware (or a combination of software and hardware) operable to communicate with the network 430. More specifically, the interface 404 can include software supporting one or more communication protocols associated with communications. As such, the network 430 or the interface's hardware can be operable to communicate physical signals within and outside of the illustrated computer 402.

The computer 402 includes a processor 405. Although illustrated as a single processor 405 in FIG. 4, two or more processors 405 can be used according to particular needs, desires, or particular implementations of the computer 402 and the described functionality. Generally, the processor 405 can execute instructions and can manipulate data to perform the operations of the computer 402, including operations using algorithms, methods, functions, processes, flows, and procedures as described in the present disclosure.

The computer 402 also includes a database 406 that can hold data for the computer 402 and other components connected to the network 430 (whether illustrated or not). For example, database 406 can be an in-memory, conventional, or a database storing data consistent with the present disclosure. In some implementations, database 406 can be a combination of two or more different database types (for example, hybrid in-memory and conventional databases) according to particular needs, desires, or particular implementations of the computer 402 and the described functionality. Although illustrated as a single database 406 in FIG. 4, two or more databases (of the same, different, or combination of types) can be used according to particular needs, desires, or particular implementations of the computer 402 and the described functionality. While database 406 is illustrated as an internal component of the computer 402, in alternative implementations, database 406 can be external to the computer 402.

The computer 402 also includes a memory 407 that can hold data for the computer 402 or a combination of components connected to the network 430 (whether illustrated or not). Memory 407 can store any data consistent with the present disclosure. In some implementations, memory 407 can be a combination of two or more different types of memory (for example, a combination of semiconductor and magnetic storage) according to particular needs, desires, or particular implementations of the computer 402 and the described functionality. Although illustrated as a single memory 407 in FIG. 4, two or more memories 407 (of the same, different, or combination of types) can be used according to particular needs, desires, or particular implementations of the computer 402 and the described functionality. While memory 407 is illustrated as an internal component of the computer 402, in alternative implementations, memory 407 can be external to the computer 402.

The application 408 can be an algorithmic software engine providing functionality according to particular needs, desires, or particular implementations of the computer 402 and the described functionality. For example, application 408 can serve as one or more components, modules, or applications. Further, although illustrated as a single application 408, the application 408 can be implemented as multiple applications 408 on the computer 402. In addition, although illustrated as internal to the computer 402, in alternative implementations, the application 408 can be external to the computer 402.

The computer 402 can also include a power supply 414. The power supply 414 can include a rechargeable or non-rechargeable battery that can be configured to be either user- or non-user-replaceable. In some implementations, the power supply 414 can include power-conversion and management circuits, including recharging, standby, and power management functionalities. In some implementations, the power-supply 414 can include a power plug to allow the computer 402 to be plugged into a wall socket or a power source to, for example, power the computer 402 or recharge a rechargeable battery.

There can be any number of computers 402 associated with, or external to, a computer system containing computer 402, with each computer 402 communicating over network 430. Further, the terms "client," "user," and other appropriate terminology can be used interchangeably, as appropriate, without departing from the scope of the present disclosure. Moreover, the present disclosure contemplates that many users can use one computer 402 and one user can use multiple computers 402.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method;

a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

EXAMPLES

In an example implementation, a system includes a laser induced breakdown spectroscopy (LIBS) system; an ultrasonic shaking plate configured to separate rock cuttings from a drilling slurry; a wireless communications system communicatively coupled to the LIBS system; and one or more processors configured to perform operations. The operations include introducing a drilling slurry including powdered rock cuttings to the ultrasonic shaking plate; operating the ultrasonic shaking plate to separate the powdered rock cuttings from the drilling slurry; capturing one or more recordings of the powdered rock cuttings using the LIBS system; determining an elemental analysis of the powdered rock cuttings based on the one or more recordings; and transmitting, by the wireless communications system, the elemental analysis to an external computing system.

In an aspect combinable with the example implementation, introducing the drilling slurry includes controlling one or more valves to enable the drilling slurry to flow to the ultrasonic shaking plate.

In another aspect combinable with one, some, or all of the previous aspects, the operations include steering drilling equipment based on the elemental analysis to access a desired portion of a subsurface formation.

In another aspect combinable with one, some, or all of the previous aspects, steering the drilling equipment includes determining that a type of rock of the powdered rock does not match a rock type of the desired portion of the subsurface formation, and in response, steering the drilling equipment to change a direction of drilling.

In another aspect combinable with one, some, or all of the previous aspects, the wireless communications system includes low latency units for fast data transmission from the LIBS system to the external computing system.

In another aspect combinable with one, some, or all of the previous aspects, the operations include generating one or more three-dimensional images of the powdered rock cuttings based on the one or more recordings from the LIBS system.

In another aspect combinable with one, some, or all of the previous aspects, the operations include determining a size of a rock cutting using the one or more three-dimensional images.

In another aspect combinable with one, some, or all of the previous aspects, the operations include determining a frequency of capturing the one or more recordings of the powdered rock cuttings based on drilling conditions of a well drill.

Another aspect combinable with one, some, or all of the previous aspects includes a fabric-based sieve coupled with the ultrasonic shaking plate to retain the powdered rock cuttings and allow liquid of the drilling slurry to pass through.

In another aspect combinable with one, some, or all of the previous aspects, transmitting the elemental analysis occurs in real-time.

In another example implementation, a method for elemental analysis of rock cutting in underbalanced coiled tube drilling includes introducing a drilling slurry including powdered rock cuttings to an ultrasonic shaking plate; operating the ultrasonic shaking plate to separate the powdered rock cuttings from the drilling slurry; capturing one or more recordings of the powdered rock cuttings using a laser-induced breakdown spectroscopy (LIBS) system; determining an elemental analysis of the powdered rock cuttings based on the one or more recordings; and transmitting, by a wireless communications system, the elemental analysis to an external computing system.

In an aspect combinable with the example implementation, introducing the drilling slurry includes controlling one or more valves to enable the drilling slurry to flow to the ultrasonic shaking plate.

Another aspect combinable with one, some, or all of the previous aspects includes steering drilling equipment based on the elemental analysis to access a desired portion of a subsurface formation.

In another aspect combinable with one, some, or all of the previous aspects, steering the drilling equipment includes determining that a type of rock of the powdered rock cuttings does not match a rock type of the desired portion of the subsurface formation, and in response, steering the drilling equipment to change a direction of drilling.

In another aspect combinable with one, some, or all of the previous aspects, the wireless communications system includes low latency units for fast data transmission from the LIBS system to the external computing system.

Another aspect combinable with one, some, or all of the previous aspects includes generating one or more three-dimensional images of the powdered rock cuttings based on the one or more recordings from the LIBS system.

Another aspect combinable with one, some, or all of the previous aspects includes determining a size of a rock cutting using the one or more three-dimensional images.

Another aspect combinable with one, some, or all of the previous aspects includes determining a frequency of capturing the one or more recordings of the powdered rock cuttings based on drilling conditions of a well drill.

Another aspect combinable with one, some, or all of the previous aspects includes filtering the powdered rock cuttings from the drilling slurry using a fabric-based sieve coupled with the ultrasonic shaking plate.

In another aspect combinable with one, some, or all of the previous aspects, transmitting the elemental analysis occurs in real-time.

What is claimed is:

1. A system comprising:
- a laser induced breakdown spectroscopy (LIBS) system;
- an ultrasonic shaking plate configured to separate rock cuttings from a drilling slurry;
- a wireless communications system communicatively coupled to the LIBS system; and
- one or more processors configured to perform operations comprising:
  - introducing a drilling slurry including powdered rock cuttings to the ultrasonic shaking plate;
  - operating the ultrasonic shaking plate to separate the powdered rock cuttings from the drilling slurry;
  - capturing one or more recordings of the powdered rock cuttings using the LIBS system;

determining an elemental analysis of the powdered rock cuttings based on the one or more recordings; and transmitting, by the wireless communications system, the elemental analysis to an external computing system.

2. The system of claim 1, wherein introducing the drilling slurry comprises controlling one or more valves to enable the drilling slurry to flow to the ultrasonic shaking plate.

3. The system of claim 1, wherein the operations further comprise steering drilling equipment based on the elemental analysis to access a desired portion of a subsurface formation.

4. The system of claim 3, wherein steering the drilling equipment comprises determining that a type of rock of the powdered rock does not match a rock type of the desired portion of the subsurface formation, and in response, steering the drilling equipment to change a direction of drilling.

5. The system of claim 1, wherein the wireless communications system comprises low latency units for fast data transmission from the LIBS system to the external computing system.

6. The system of claim 1, wherein the operations further comprise generating one or more three-dimensional images of the powdered rock cuttings based on the one or more recordings from the LIBS system.

7. The system of claim 6, wherein the operations further comprise determining a size of a rock cutting using the one or more three-dimensional images.

8. The system of claim 1, wherein the operations further comprise determining a frequency of capturing the one or more recordings of the powdered rock cuttings based on drilling conditions of a well drill.

9. The system of claim 1, further comprising a fabric-based sieve coupled with the ultrasonic shaking plate to retain the powdered rock cuttings and allow liquid of the drilling slurry to pass through.

10. The system of claim 1, wherein transmitting the elemental analysis occurs in real-time.

11. A method for elemental analysis of rock cutting in underbalanced coiled tube drilling, the method comprising:

introducing a drilling slurry including powdered rock cuttings to an ultrasonic shaking plate;

operating the ultrasonic shaking plate to separate the powdered rock cuttings from the drilling slurry;

capturing one or more recordings of the powdered rock cuttings using a laser-induced breakdown spectroscopy (LIBS) system;

determining an elemental analysis of the powdered rock cuttings based on the one or more recordings; and transmitting, by a wireless communications system, the elemental analysis to an external computing system.

12. The method of claim 11, wherein introducing the drilling slurry comprises controlling one or more valves to enable the drilling slurry to flow to the ultrasonic shaking plate.

13. The method of claim 11, further comprising steering drilling equipment based on the elemental analysis to access a desired portion of a subsurface formation.

14. The method of claim 13, wherein steering the drilling equipment comprises determining that a type of rock of the powdered rock cuttings does not match a rock type of the desired portion of the subsurface formation, and in response, steering the drilling equipment to change a direction of drilling.

15. The method of claim 11, wherein the wireless communications system comprises low latency units for fast data transmission from the LIBS system to the external computing system.

16. The method of claim 11, further comprising generating one or more three-dimensional images of the powdered rock cuttings based on the one or more recordings from the LIBS system.

17. The method of claim 16, further comprising determining a size of a rock cutting using the one or more three-dimensional images.

18. The method of claim 11, further comprising determining a frequency of capturing the one or more recordings of the powdered rock cuttings based on drilling conditions of a well drill.

19. The method of claim 11, further comprising filtering the powdered rock cuttings from the drilling slurry using a fabric-based sieve coupled with the ultrasonic shaking plate.

20. The method of claim 11, wherein transmitting the elemental analysis occurs in real-time.

* * * * *